US007030132B2

(12) United States Patent
Schellens et al.

(10) Patent No.: US 7,030,132 B2
(45) Date of Patent: Apr. 18, 2006

(54) METHOD OF IMPROVING BIOAVAILABILITY OF ORALLY ADMINISTERED DRUGS, A METHOD OF SCREENING FOR ENHANCERS OF SUCH BIOAVAILABILITY AND NOVEL PHARMACEUTICAL COMPOSITIONS FOR ORAL DELIVERY OF DRUGS

(75) Inventors: Johannes Henricus Matthias Schellens, Kockengen (NL); Alfred Hermanus Schinkel, Amsterdam (NL)

(73) Assignee: Cancer Research Ventures Limited, London (GB)

( * ) Notice: Subject to any disclaimer, the term of this patent is extended or adjusted under 35 U.S.C. 154(b) by 402 days.

(21) Appl. No.: 09/988,285

(22) Filed: Nov. 19, 2001

(65) Prior Publication Data

US 2002/0128282 A1 Sep. 12, 2002

Related U.S. Application Data

(63) Continuation-in-part of application No. PCT/NL00/00331, filed on May 17, 2000.

(30) Foreign Application Priority Data

May 17, 1999 (NL) .................................. 1012066
Jun. 30, 1999 (NL) .................................. 1012481

(51) Int. Cl.
  *A61K 31/44* (2006.01)
  *A61K 31/56* (2006.01)
(52) U.S. Cl. ...................................... 514/297; 514/179
(58) Field of Classification Search ................ 514/297, 514/179
  See application file for complete search history.

(56) References Cited

U.S. PATENT DOCUMENTS

| 5,567,592 A | 10/1996 | Benet et al. |
| 5,604,237 A | 2/1997 | Dumaitre et al. |
| 5,663,179 A | 9/1997 | Dumaitre et al. |
| 5,786,344 A | 7/1998 | Ratain et al. |
| 5,958,937 A | 9/1999 | Hausheer et al. |
| 6,004,927 A | 12/1999 | Benet et al. |
| 6,028,054 A | 2/2000 | Benet et al. |
| 6,248,891 B1 | 6/2001 | Sharp et al. |
| 6,469,022 B1 | 10/2002 | Schellens |
| 6,521,635 B1 | 2/2003 | Bates et al. |

FOREIGN PATENT DOCUMENTS

| EP | 0 098 098 A2 | 1/1984 |
| EP | 0 494 623 A1 | 7/1992 |
| WO | WO 92/12132 A1 | 7/1992 |
| WO | WO 94/01408 A1 | 1/1994 |
| WO | WO 96/11007 A1 | 4/1996 |
| WO | WO 97/15269 A2 | 5/1997 |
| WO | WO 98/53811 A1 | 12/1998 |
| WO | WO 99/40110 A1 | 8/1999 |
| WO | WO 99/65493 A1 | 12/1999 |
| WO | WO 00/07605 A1 | 2/2000 |

OTHER PUBLICATIONS

Rabindran et al., Cancer Research, 58, 5850-5858, Dec. 15, 1998.
Hazlehurst et al., Cancer Research, 59, 1021-1028, Mar. 1, 1999.
B. Kuska, Journal of the National Cancer Institute, vol. 91, No. 5, 402-404, Mar. 3, 1999.
Ross et al., Journal of the National Cancer Institute, vol. 91, No. 5, 429-433, Mar. 3, 1999.
K. Miyake et al., Cancer Research, Jan. 1, 1999, vol. 59, pp. 8-13.
Allikmets et al., Cancer Research, 58, 5337-5339, Dec. 1, 1998.
Doyle et al., Proc. Natl. Acad. Sci. USA, vol. 95, pp. 15665-15670, Dec. 1998.
Palmer et al., J. Med. Chem. 1988, 31, 707-712.
Denny et al., J. Med. Chem. 1987, 30, 658-663.
Sparreboom et al., Anticancer Drugs, 10(8): 719-728, Sep. 1999.
de Bruin et al., Cancer Letters, 146 (1999) 117-126.
Hyafil et al., Cancer Research, 53, 4595-4602, Oct. 1, 1993.
Karato et al., Journal of Clinical Oncology, vol. 11, No. 10, pp. 2030-2035, Oct. 1993.
Slichenmyer et al., J. Natl. Cancer Inst., vol. 85, No. 4, pp. 271-291, 1993.
Sikic et al., 12th Bristol Myers Squibb Nagoya International Cancer Treatment Symposium, Oct. 4-5, 1996, Nagoya, Japan, pp. S13-S19.
Sparreboom et al., Proc. Natl. Acad. Sci. USA, vol. 94, 2031-2035, Mar. 1997.
Rabindran et al., Proceedings of the American Association for Cancer Research-Annual Meeting, Mar. 1999, vol. 40, pp. 315-316, Abstract #2093.
International Search Report.
Rabindran, S.K., "Fumitremorgin C reverses a novel multidrug resistance mechanism in mitoxantrone-selected cells", Wyeth-Ayerst Research, XP-000878953.
Rabindran, S.K., "Reversal of a Novel Multidrug Resistance Mechanism in Human Colon Carcinama Cells by Fumitremorgin", Cancer Research 585850-5858, Dec. 15, 1998, XP-000876633.

(Continued)

Primary Examiner—Kevin E. Weddington
(74) Attorney, Agent, or Firm—Birch, Stewart, Kolasch & Birch LLP

(57) ABSTRACT

A method for increasing the systemic exposure of cells selected from tumor cells and normal cells to an orally administered pharmaceutically active compound, wherein a bioenhancer comprising an inhibitor of BCRP is orally administered concomitantly with said orally administered pharmaceutically active compound, and in which method the inhibitor is administered simultaneously with the pharmaceutical compound.

13 Claims, 2 Drawing Sheets

OTHER PUBLICATIONS

Hazlehurst, L.A., "Multiple Mechanism Confer Drug Resistance to Mitoxantrone in the Human 8226 Myeloma Cell Line", Cancer Research 59, 1021-1028, Mar. 1, 1999, XP-000876632.

Scheffer et al., Cancer Research 60, 2589-2593, May 15, 2000.

Maliepaard et al., Cancer Research 59, 4559-4563, Sep. 15, 1999.

Allen et al., Cancer Research 59, 4237-4241, Sep. 1, 1999.

Rabindran et al., Cancer Research 60, 47-50, Jan. 1, 2000.

M. Brangi et al., Cancer Research 59, 5938-5946, Dec. 1, 1999.

M.D. DeMario et al., Journal of Clinical Oncology, vol. 16, No. 7, Jul. 1998, pp. 2557-2567.

METHOD OF IMPROVING BIOAVAILABILITY OF ORALLY ADMINISTERED DRUGS, A METHOD OF SCREENING FOR ENHANCERS OF SUCH BIOAVAILABILITY AND NOVEL PHARMACEUTICAL COMPOSITIONS FOR ORAL DELIVERY OF DRUGS

CROSS REFERENCE TO RELATED APPLICATION

This is a Continuation-in-Part of International Application PCT/NL00/00331, with an international filing date of May 17, 2000, which was published under PCT Article 21 (2) in English, and the complete disclosure of which is incorporated into this application by reference.

SUMMARY OF THE INVENTION

The subject invention is directed at a method of improving bioavailability of orally administered drugs. The invention further covers a method of screening for enhancers of bioavailability of orally administered drugs. The invention also covers application of the bioenhancer in pharmaceutical compositions for oral delivery of drugs, thereby providing novel and improved pharmaceutical compositions. In this patent application, "bioavailability" is interchangeably used with the term "systemic exposure", i.e. the bioavailability of a drug is expressed as the systemic exposure of a cell to drugs.

BACKGROUND OF THE INVENTION

The bioavailability of drugs is a complex issue. For a long time efforts were focussed on the processes occurring in the liver when addressing the issue of bioavailability of drugs. All blood from the gastrointestinal tract passes the liver before going anywhere else in the body. Thus, first pass effect of the liver was thought to be of great influence on bioavailability. Certainly it was thought to be of more influence than any mechanism exerted by the gut. This was thought to be the case for example due to the much lower presence of cytochrome P450 in the gut as compared to the liver. It was known for a fact that cytochrome P450 catalyses phase I biotransfornation, i.e. the process involved in removal of drugs from the body. In phase II, the subsequent step of the removal process, a hydrophilic group is added in order to increase solubility and thus subsequently speed up elimination through bile or kidneys.

Traditionally, efforts have thus been focussed on increasing solubility and membrane permeability when addressing the problem of bioavailability of drugs. Most particularly, metabolism-associated approaches have been focussed on the liver biotransformation process. The problem with these approaches has, however, been the broad effects on liver metabolism in general and thus broad non-specific and often thus undesirable systemic effects.

Recently however, it has been suggested that the absorption across intestinal epithelia also affect bioavailability of drugs. The enterocyte membrane contains numerous transport proteins that carry nutrients from the lumen of the gut into the enterocytes. Active or passive transport through the membrane is responsible for the passage of many molecules through the membrane into the cytoplasm. The nutrients, and also drugs, subsequently pass through the enterocytes into the capillary net and proceed to the circulation system and the liver.

However, the intestine can also remove compounds from the cytoplasm of enterocytes and transport these compounds back to the lumen. Presumably this is a mechanism that has evolved to protect against potentially damaging compounds that enter the body via the oral route. Following this line of reasoning, U.S. Pat. No. 5,567,592 (equivalent to WO 95/20980) suggests that two gut related mechanisms could be inhibited in order to increase the net flux of drug from the gut. On the one hand an inhibitor of cytochrome P450, in particular inhibitors of the cytochrome P 450 3A (CYP3A) is suggested and on the other hand use of an inhibitor of P-glycoprotein (P-gp) or a combination of the two categories of inhibitors is suggested. It is worth noting that inhibitors of P-gp and CYP3A are extensively disclosed in the prior art. Moreover, inhibitors of CYP3A are generally hydrophobic compounds that can pass cell membranes without the need of transport proteins.

P-glycoprotein back transport activity in the gut of a mammal can be inhibited with a view to increasing drug bioavailability by virtue of the fact that the net transport of drugs through the enterocyte layer will be enhanced. P-glycoprotein is located inter alia in the small intestine and colon on the luminal side of epithelial cells and transports dietary toxins back into the lumen and thus helps prevent the toxins being absorbed into the portal circulation.

U.S. Pat. No. 5,567,592 does, however, not illustrate or give a specific example of a P-gp inhibitor. Nor does it provide any information on success of the chosen method. The document merely shows an increase in cyclosporin bioavailability caused by co-administration of ketoconazole. Ketoconazole is a cytochrome P450 3A inhibitor.

A later document (The Lancet, Vol. 352, Jul. 25, 1998) describes how coadministration of cyclosporin enables oral therapy with paclitaxel in patients. Normally, orally introduced paclitaxel is poorly bioavailable due to the exceedingly high affinity thereof for the multidrug transporter P-glycoprotein which is abundantly present in the gastrointestinal tract (Trends Genet. 1997; 13:217–22, Cell 1994; 77: 491–502). Studies in mdr1a (−/−) knock out mice lacking P-gp revealed an increased uptake of paclitaxel (Proc. Natl. Acad. Sci. U.S.A. 1997; 4:2031–35) Subsequently, it was thus described (British Journal of Cancer 1997; 76: 1181–1183) in how paclitaxel was orally introduced into wild type mice together with the P-gp blocker SDZ PSC 833 or the P-gp blocker cyclosporin (Clinical Cancer Research 1998; 4: 2293–2297) resulting in a tenfold increased systemic exposure to paclitaxel. Proof of concept tests were subsequently carried out on patients (The Lancet, Vol. 352, Jul. 25, 1998) and confirmed the results. Co-administration of paclitaxel with cyclosporin increased the absorption of oral paclitaxel to therapeutic plasma concentrations.

The P-gp is known from its association with multi drug resistance development of tumor cells. A number of other transport proteins have also been associated with multi drug resistance (MDR) such as the MRP (multidrug resistance associated protein) and possibly the MVP (major vault protein). An alternative system also leading to MDR is the interference of some drugs in the ability of the cell to enter apoptosis for example cells genetically deficient in p53 or cells overexpressing bclxL. Both MRP and P-gp belong to the group of proteins classified as ABC proteins. ABC proteins function by way of their being ATP binding proteins. The phenomenon of multi drug resistance consists of tumor cells exhibiting resistance to a large number of structurally unrelated antineoplastic agents. These agents include anthracyclines, vinca alkaloids, taxol and epipodophyllotoxins. ATP hydrolysis on the cytoplasmic face of P-gp is required for transport of hydrophobic compounds from a tumor cell. The addition of verapamil, diltiazem, quinine, trifluoperazine or cyclosporin seems to potentially reverse P-gp asssociated MDR.

It should be noted that in spite of extensive knowledge of these MDR mechanisms in iii vitro systems in many tumors, it is still unclear what mechanisms contribute most to the multi drug resistance in the clinical setting. It is quite possible that other unidentified or poorly understood MDR mechanisms will turn out to be at least as important as the MDR mechanisms defined above.

In this respect we point to a new protein that has been found. The protein is called Breast Cancer Resistance Protein or BCRP. It is also known as MXR or ABCP. A number of recent publications have illustrated that this protein is also a drug resistance related protein. A number of such disclosures are provided in the Proceedings of the American Association for Cancer Research volume 40, March 1999. e.g. Rocchi et al. Abstract 2090, Zhan et al. Abstract 2091, Ross et al. Abstract 2092, Rabindran et al. Abstract 2093, Litman et al. Abstract 4413, Schlegel et al. Abstract 4415, Rohde et al. Abstract 4417 and Rabindran et al., Cancer Research 1998; 58: 5850–5858.

The amino acid sequence of BCRP has been determined and the gene has been isolated and sequenced (Doyle et al. Proc. Natl. Acad. Sci USA 1998; Vol 95; 15665–15670 and WO 99/40110). It has been determined to be an ABC transport protein. The P-gp protein is also an ABC protein, but differs significantly from the BCRP. This is clearly illustrated by the sequence data and also by the fact that the presence of verapamil (an inhibitor of P-gp) did not prevent drug resistance for doxorubicin in cells overexpressing BCRP. The doxorubicin resistance was subsequently attributed to the overexpression of this protein. Thus cells exhibiting doxorubicin resistance can possess either P-gp and/or BCRP transport mechanisms. Also on the other hand P-gp overexpressing cells exhibit resistance to paclitaxel and vincristine. No resistance to these compounds is however present when the P-gp mechanism is inactive and the BCRP mechanism is active. Thus there are clearly two different systems of drug resistance with different proteins that show different specificities to drugs.

Rabindran et al. (Proc. Am. Assoc. Cancer Res.; 40: abstract 2093 and Cancer. res. 1998; 58: 5850–5858) disclose that the mycotoxin fumitremorgin C (FTC) reverses in vitro non-P-gp, non-MRP-mediated MDR in mitoxantrone-selected cells derived from a human colon carcinoma cell line. It was found that FTC did not reverse MDR in cells overexpressing P-gp or MRP. It was therefore suggested that this reversal of non-P-gp, non-MRP-mediated MDR involved a transport protein, possibly BCRP, having substrate specificities substantially different from those of P-gp and MRP. Such a suggestion can merely be considered speculative in view of the complexity of the issues as is illustrated on page 5857 of this article, second paragraph where it is stated that "the mechanism by which FTC reverses drug resistance is unknown". This article is further silent regarding any link between BCRP and non-tumor cells. In addition, in vivo data are not provided.

Hazlehurst et al. (Cancer. Res. 1999; 59: 1021–1027) disclose that at low levels of MDR FTC reverses in vitro MDR in mitoxantrone-selected cells derived from the P-pg negative human myeloma cell line 8226. This reversal was attributed to BCRP. However, at higher levels of MDR several other drug-resistant mechanisms can be involved including non-transport phenomena as evidenced by reduced topoisomerase II levels and activity. It remains therefore uncertain whether the reversal can in fact be attributed specifically to BCRP and certainly is uncertain in the case of higher levels of MDR then were tested. Regarding this issue it is worth noting that increasing the degree of resistance to mitoxantrone in the human 8226/MR20 myeloma cell line from 10 to 37 times did not further reduce the intracellular drug concentration. Additionally, there is no suggestion or teaching of BCRP in relation to non-tumor cells. Furthermore, in vivo data are not provided.

Consequently, the prior art only relates to MDR in tumor cells and is silent about drug transport in normal cells. Additionally, much speculation exists about the mechanisms involved in MDR. Furthermore, the studies are limited to in vitro systems. Forms of administration of drugs, in particular oral administration of drugs, in relation to drug transport in normal cells, is not addressed.

WO 99/40110 (priority date 5 Feb. 1998, published 12 Aug. 1999; WO 99/40110 is a non-prepublished patent application and therefore only relevant for novelty) discloses BCRP that is overexpressed in breast carcinoma cell lines, inhibitors of BCRP such as immunoglobulins (e.g. antibodies) and non-immuno-globulins (e.g. organic compounds such as FTC). Example 14 shows the beneficial effect of FTC on the intercellular concentration of BBR 3390 in MCF-7 cells (a human breast carcinoma cell line). There is no disclosure of the oral administration of BCRP inhibitors together with pharmaceutical compounds to enhance the bioavailability of the latter. There is no link mentioned between normal tissue, i.e. healthy tissue, and BCRP. Additionally, only in vitro data are provided for the effect of FTC on the inter- and intracellular BBR 3390 concentrations in MCF-7 cells.

Notwithstanding the lack of data concerning the BCRP and the mechanism of transport, it was decided to investigate whether it could be a useful target to approach with a view to increasing oral bioavailability of drugs. An analogous line of reasoning to that employed for P-gp was followed, however, without any detailed knowledge of the mechanism to be inhibited and the potential consequences thereof for the cell or more importantly the patient. Furthermore, there was no knowledge on whether the effect would be high enough to show any effect on the drug distribution. Neither was there any knowledge whether inhibition of such a transport system would result in activation of another system. Nor was there any indication whether the inhibition would be more harmful than beneficial. Due to the large differences between P-gp and BCRP and lack of knowledge concerning the transport mechanism, there was no reasonable expectation of success that the BCRP system might function analogously to that of P-gp and thus that inhibition thereof could increase oral drug delivery without potentially seriously disrupting the normal cellular processes and thus potentially being detrimental to the patient.

DESCRIPTION OF THE INVENTION

Figure 1:
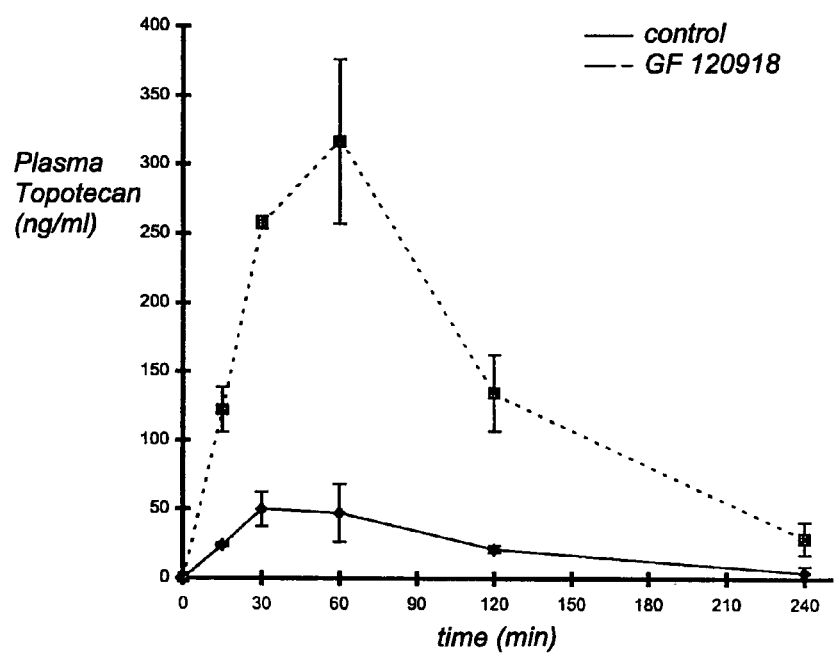
FIG. 1 is a graph of the topotecan levels over time in plasma as determine by HPLC.

Using the recently developed monoclonal antibody BXP-34 against BCRP (Scheffer et al., "BCRP is localized at the plasma membrane in mitoxantrone and topotecan resistant cell lines"; Cancer Res., in press), it was shown that BRCP protein is expressed in endothelium of virtually every vein and capillary. Furthermore, high levels of BCRP protein were observed in placenta, mainly in the synchytiotrophoblast. BCRP was also found to be present in liver, small intestine and colon. These results were highly indicative that BCRP is involved in the regulation of uptake of BCRP substrates from the gastrointestinal tract and may have a function for the fetus. BRCP was further found to be expressed in the blood-brain barrier and the protective role of BCRP is therefore believed to encompass the brain as well.

In vitro studies revealed that cells overexpressing BCRP are resistant to a large and varied number of compounds. Camptothecin and derivatives thereof in particular topotecan, SN38 (an active metabolite of CPT11, also known as irinotecan), GG211 (GF147211, also known as NX211), DX8951f, BNP1350, 9-aminocamphotecin, 9-nitrocamphotecin and mitoxantrone are examples thereof.

We subsequently tested a number of compounds selected therefrom that also exhibit low bioavailability to see if we could enhance their bioavailability after oral dosage. In order to assess this we combined their oral dosage in mdr1a/1b P-gp negative mice with BCRP inhibitors. Bioavailability is defined as the total amount of drug systemically available over time. The test compares the amount of drug systemically available when administered in the presence and in the absence of a BCRP inhibitor. Naturally all variables should be kept identical as much as possible e.g. amount of drug dosed and the form in which it is dosed. The measurement of the systemic amount can occur in any known manner for bodily fluid e.g. blood, serum, plasma or tissue bathed by systemic fluid e.g. skin. Urine can also be used for non metabolised drug testing.

The invention therefore relates to a method for increasing the systemic exposure of cells selected from tumor cells and normal cells to an orally administered pharmaceutically active compound, wherein a bioenhancer comprising an inhibitor of BCRP mediated and/or related drug transport is orally administered concomitantly with said orally administered pharmaceutically active compound. Preferably, the inhibitor is administered simultaneously with the pharmaceutical compound.

The compounds to be assayed for bioavailability were selected from a range of well-known cytostatic drugs. Examples of compounds tested are topotecan, GG211, DX8951f, BNP1350, 9-aminocamphotecin, 9-nitrocamphotecin and irinotecan. These are thus examples of indolizinoquinoline (in particular camptothecin) derivatives, quinazoline derivatives e.g. prazosin and anthraquinone derivatives e.g. mitoxantrone. A broad spectrum of compounds with varying lipophilicity, solubility and hydrophobicity has thus been tested. The group can be considered representative for a large number of naturally occurring toxins. However not only naturally occurring toxins are envisaged as compounds whose bioavailability after oral dosage can be increased according to the subject invention. Basically the bioavailability after oral dosage of any compound that is subject to BCRP transport can be improved. It is relatively easy for the skilled person to assess whether a compound is subject to BCRP related and/or mediated transport. The skilled person can assess in a model system whether uptake of a specific compound to be tested is low when said model system consists of a cell or organism overexpressing BCRP. Numerous tumor types like that are commonly known e.g. breast tumors (MCF-7/AdrVp), colon carcinoma (S1, HT29), gastric carcinoma's (EPG85-257), fibrosarcoma (EPF86-079) and myeloma (8226) origin (Proceedings of the American Association for Cancer Research, vol. 40, March 1999, e.g. Miyake et al. Abstract 2089 and Ross et al. Abstract 2092) as well as from tumor cell derived cell-lines such as T8 and MX3 derived from the human ovary-cancer cell-line IGROV-1 such as described by Maliepaard et al., Proceedings for the American Association for Cancer Research vol. 40, March 1999, Abstract 4416, and Cancer Res.1999; 59: to be published). One can additionally test the drug in a system known to exhibit one or more other types of drug transporters in order to assess whether the compound is subject to only BCRP related transport or multiple forms of transport. In the latter case it will be preferable to either use an inhibitor capable of blocking not only BCRP related transport but also the relevant other system and/or dosing a number of inhibitors specific for each relevant transport system. Alternatively one can also merely assess whether the compound to be tested exhibits binding to the BCRP protein as being indicative for involvement of BCRP in the transport thereof.

There are a number of inhibitors of BCRP known to be available. These compounds have varying specificity toward BCRP and also towards other proteins such as P-gp The compound 9,10-dihydro-5-methoxy-9-oxo-N-[4-[2-(1,2,3,4-tetrahydro-6,7dimethoxy-2-isoquilonyl)ethyl-4-phenyl]-4-acridinecarboxamide (compound I; also known as GF120918 and GG918) was tested. The molecular structure of this compound is shown below.

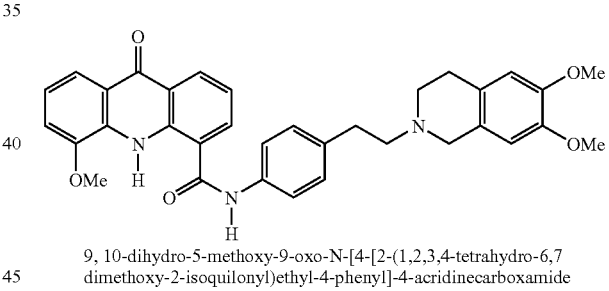

9, 10-dihydro-5-methoxy-9-oxo-N-[4-[2-(1,2,3,4-tetrahydro-6,7 dimethoxy-2-isoquilonyl)ethyl-4-phenyl]-4-acridinecarboxamide This compound is known to also inhibit P-gp related transport in tumor cells exhibiting P-gp overexpression in vitro. Other compounds that were tested are XR9051 and XR 9576 from Xenova. Another BCRP inhibitor is fumitremorgin C (FTC), which is a mycotoxin. Other mycotoxins can also be used as bioenhancer. FTC is an example of a compound that has no effect on P-gp related transport. A further example known to exhibit inhibition of BCRP is BIB-F. A compound of further interest is cyclosporin A. These compounds are available to the skilled person and are disclosed in a number of publications that are incorporated by reference. The references are Schlegel et al. Abstract 4415, Proc. Am. Ass. Cancer Res. Vol. 40; March 1999: 669 and Rabindran et al. Abstract 2093 ibid., pag 315. Clearly the following categories of compounds can thus be considered to provide BCRP inhibitors of varying specificity: acridine derivatives, quinoline derivatives in particular isoquinoline derivatives and combinations thereof.

Alternative inhibitors can be found quite readily by the skilled person. An alternative suitable source of inhibitor could for example be provided by monoclonal antibodies raised specifically against BCRP. Recombinant BCRP producing clones could be used as a source of protein against which monoclonal antibodies could be raised in a manner known per se for raising monoclonal antibodies against recombinant protein and in a manner known per se for producing recombinant protein. As stated elsewhere the genetic information encoding BCRP is available and thus the methodology for expression of the protein is clear to the skilled person.

Monoclonal antibodies would be a very specific inhibitor of BCRP and as such form a preferred embodiment of the group of inhibitors to be used. A less specific inhibitor could be an ATP-ase, preferably a BCRP-ATP-ase specific inhibitor. Such a compound would inhibit the ATP related activity of the protein and thus prevent transport.

The BCRP inhibitor is in particular destined to inhibit drug back flux from the blood or epithelial lumen. Thus the return of drugs absorbed into the cytoplasm of enterocytes back to the lumen of the gut is inhibited. Due to the fact that the BCRP is not only present in the intestine but also located elsewhere, the BCRP transport for these other locations may also be affected. However the effect will be highest in the intestine due to the oral dosage of the inhibitor. Preferably the bioenhancer, i.e. the inhibitor of BCRP, will bind BCRP quickly and inhibit while the drug is passing through the enterocyte. The inhibitor can be reversible or irreversible. If it is reversible, the bioenhancer will pass through the liver and be removed. In addition, the natural protective activity of the BCRP system against dietary toxins will be returned sometime after the oral dosage has occurred. The bioenhancer can act as a competitive, non-competitive, mixed or an irreversible inhibitor. It can be transportable or non-transportable. It can bind to or interact with the BCRP on cytoplasmic accessible surface, any membrane-spanning domain, and any ATP binding site. By interacting with BCRP it is possible to prevent binding of ATP.

Suitably, a bioenhancer can be selected from substances that are related to known substrates for BCRP. Suitable bioenhancers could be derivatives of acridine, quinoline, isoquinoline, indolizino-quinoline, camptothecin, anthraquinone, quinazoline, bisanthrene and rhodamine. Alternatively, a bioenhancer can be selected from vinca alkaloids, fatty acids, triazoles, taxol and derivatives thereof, pyrrolidones, piperazines, piperidines, pyridines, pyridones, pyrrolidines, retinoids, salicylates, sorbitans, phenothiazines, polyethylene glycols, colchicine, cephalosporines, cannabioids, cyclic peptides, flavones, flavenoids, opioids, phenylalkylamines, aminoacridines, aminoquinolines, anilides, anthracyclines, antibiotics, antiestrogens, imidazoles, (iso) quinolines, benzofurans, benzodiazepines, benzhydryl compounds, benzazepines, dibenzazepines, epipodophyllotoxins, macrolides, rauwolfia alkaloids, and steroids. Preferably, compounds that do not exhibit sufficient affinity for P-gp to exert increased bioavailability due to an effect on the P-gp transport system are applied. Suitably, a P-gp binding bioenhancer also exhibiting specificity for BCKP sufficient to increase bioavailability of a drug not susceptible to transport via the P-gp mechanism is applied in combination with such a drug or in a cell type free of a P-gp system.

The amount to be dosed will depend on the drug it is to be combined with, the type of disease to be combated, the pharmacological acceptability of the dosage, the size gender and age of the patient etc. All factors commonly known to be of pharmacological interest and a matter of routine for the skilled person to determine on a case by case basis. Numerous assays are available to determine best dosage regimes.

Suitably, the maximal increase in bioavailability needs to be achieved. Thus, such a combination of drug and inhibitor is preferably selected. Once it has been ascertained a particular drug can undergo increased bioavailability, it then becomes possible to reduce the dosage required to be orally administered to achieve the desired medicinal effect. Thus the amount of drug to be administered can be reduced. It thus becomes possible to administer lower dosage forms of known drugs. It also becomes possible to orally administer drugs that previously were not orally administered due to extreme side effects or toxicity at the high levels required to achieve reasonable or effective serum concentrations. Also it is most likely that an increase in bioavailability will result in a lowered variability of the availability of orally administered compounds, thereby enabling the use of otherwise unreliable medication. Suitably, the bioavailability is increased by at least 10%. Preferably an even higher amount e.g. more than 20% even more than 30% is achieved. Naturally as high an increase as possible is the objective.

It now becomes possible to selectively enhance BCRP mediated and/or related transport. This can be achieved by selecting an inhibitor with a higher affinity for BCRP than any other drug transport related protein present in the gastrointestinal tract or cells associated with the oral trajectory of drugs that affect bioavailability, preferably, an inhibitor having a higher affinity for BCRP than for P-gp mediated and/or related transport. Specifically, one can think of a bioenhancer that inhibits BCRP mediated or related transport better than other multi drug resistance related drug transport. Such a bioenhancer is suitably better at inhibiting BCRP related or mediated transport than P-gp mediated or related transport. Also one can envisage the specificity being better for BCRP than for MRP and/or MVP. Suitably one or more combinations can also be envisaged. Also a bioenhancer can be envisaged inhibiting only BCRP mediated and/or related drug transport and not affecting any of the other systems. According to the invention, the $IC_{50}(BCRP)/IC_{50}(other\ transport\ protein)$ is at least less than 1, preferably less than 0.7, more preferably less than 0.3 and most preferably less than 0.1.

BCRP mediated and/or related transport is to be understood as the demonstrated transport of a drug in a BCRP negative cell in which BCRP cDNA is expressed through transfection.

The selected inhibitor will depend also on the selection of drug to be administered. It is known that some drugs are only transported by one mechanism, some by more than one, and some by a multitude of systems. Obviously, where more than one system is involved either numerous specific inhibitors or a generally applicable inhibitor will be preferred to achieve maximal effect.

The best way to assess the desired combination is on the basis of assays. It is difficult to predict on the basis of molecular structure what combination to use. It is also difficult to assess by molecular structure alone whether a drug or bioenhancer will be BCRP specific or have a broader spectrum of activity. However, molecular designing will be able to assist in selecting suitable inhibitors.

Suitable bioassays to search for inhibitors are described in U.S. Pat. No. 5,567,592, references cited therein and in the references cited in the subject patent description. The tests to be used will be readily apparent to the skilled person. Everted gut assays, selection of inhibitor using cell growth assays, brush border membrane assays, drug uptake assays using fluorescence ATP-ase assays.

The relative ability of compounds to act as bioenhancers can be assessed using in vitro and/or in vivo drug transport measurements. Numerous systems are available that can be used as such or need some adaptation to be BCRP specific when so desired. Such adaptations can, however, be envisaged by the person skilled in the art. The activity of BCRP related or mediated transport can be measured as amount of ATP dependent transport in a system comprising BCRP and optionally being free of one or more other active ATP dependent transport systems. It can also be measured as drug dependent ATP hydrolysis. The activity can be measured using electrodes or dye, either chemically sensitive or voltage sensitive. Also numerous in vivo tests can be envisaged, analogous to those carried out for the MDR system assessment vis a vis resistance and sensitivity. The use of a knock out test animal in which the BCRP gene has been inactivated is envisaged. Such a knock out animal is also subject of the invention.

The tests with mice assessed the bioavailability of the drug in mdr1a/1b double knock out mice in the presence and the absence of a BCRP inhibitor. The bioavailability tests can also be carried out with either MRP and/or P-gp knock out mice thus enabling assessment of whether any effect found due to the presence of the bioinhibitor is due solely to BCRP, not due to P-gp and/or MRP. Thus it can be determined whether the particular drug transported is transported using one or more transport systems. The drug to be transported can be provided with a detectable marker to assess where it is located and to be able to quantitate it. Some drugs can be detected and quantitated in plasma without use of a detectable marker. The methodology employed is analogous to that disclosed in the Lancet article discussed above and is also described in Br. J. Cancer 1997, 76: 1181–1183. The methodology is thus considered to be incorporated by reference and is considered enabled to a person skilled in the art.

We found a sixfold increase in the systemic bioavailability of the tested drug when dosed together with an inhibitor of BCRP in P-gp negative mice whereas in wild type mice a ninefold increase was found (Jonker el al., submitted for publication in Nature Med.). We further found similar effects with the murine analogue of BCRP, i.e. Bcrp1, when Bcpr1 was orally co-administered with the Bcpr1 inhibitor GF120918 (Allen et al., Cancer Res. 1999; 59: 4237–4241; De Bruin et al., Cancer Res. 1999; 59: 4559–4563; Jonker et al., submitted for publication in Nature Med.) and Bcpr1 to P-gp negative mice showed a sixfold increase whereas with wild type mice.

It will be understood by the person skilled in the art that the invention in particular relates to the inhibition of BCRP. The level of MDR is dependent from the level at which BCRP is expressed. High expression levels of BCRP give rise to high levels of MDR. In the absence of a proper definition, a high level of MDR is here defined as the degree of resistance to mitoxantrone in the human 8226/MR20 myeloma cell line of more than 10 (cf. Hazlehurst et al, Cancer Res., 1999; 59: 1021–1027 cell line).

Furthermore, it will be understood by the person skilled the art that the invention relates to tumor cells and non-tumor cells, i.e. that the invention not only provides a method for enhancing the bioavailability of an orally administered drug in tumor cells, but in particular in non-tumor tissue, e.g. normal or healthy tissue.

In addition to the actual use of the combination of bioenhancer and pharmaceutically active treatment for increasing the bioavailability of the pharmaceutical compound, novel pharmaceutical compounds are also covered by the invention. It is noted that in this description pharmaceutical compounds and pharmaceutical compositions are sometimes used as alternative definitions. However, it will be apparent to the person skilled in the art that where pharmaceutical compounds are mentioned, these compounds may obviously be comprised by a pharmaceutical composition.

The invention covers pharmaceutical compositions in an embodiment for oral administration, said composition comprising a pharmaceutically active compound and a bioenhancer, said bioenhancer being an inhibitor of BCRP mediated or related transport. The pharmaceutical composition according to the invention may comprise the pharmaceutically active compound in lower dosages than normally administered when the pharmaceutically active compound is administered on its own, i.e. without the BCRP inhibitor. For the use in increasing bioavailability the two components do not necessarily have to be administered concomitantly but they must be present in the subject to be treated at overlapping periods of time. Preferably, they are present in the gut concomitantly. Any of the combinations disclosed above for the embodiments of the bioenhancer and the pharmaceutically active compound, i.e. the drug to be delivered in a combination in a pharmaceutical composition, is covered by the invention. Use of such a combination in a preparation of a medicament for improved oral delivery of the pharmaceutically active compound by means of inhibition of BCRP mediated or related transport system is also covered. It is preferable to present a combination in order to ensure maximum presence of the bioenhancer with the pharmaceutically active compound to be delivered. It is preferred that the composition be formulated such that the bioenhancer is released in the gut together with the pharmaceutically active compound or a little before the pharnaceutically active compound is released. The pharmaceutical composition may further comprise a pharmaceutically acceptable carrier. The composition is preferably sterile. Furthermore, it is preferably organoleptically acceptable. Existing pharmaceutical compositions inadvertently already disclosed that comprise the combination of a BCRP inhibitor and a pharmaceutically active component for treating or preventing a disease or pathological condition are not intended to be covered by the pharmaceutical composition claimed according to the invention. The pharmaceutically active compound can be a cytostatic drug or any non cytostatic drug. Any known drug requiring improved oral bioavailability can be incorporated. A combination of either a BCRP specific inhibitor with one or more transport inhibitors and a pharmaceutically active compound or a BCRP specific pharmaceutical compound, i.e. not using the P-gp transport system, in combination with a BCRP inhibitor also falls within the preferred embodiments.

Besides the above, the invention also covers a method of screening for pharmaceutically active compounds that are transported via the BCRP transport system. The invention also covers a method for screening for inhibitors of BCRP mediated or related drug transport. The methods of screening occur in an analogous manner to the process described for P-gp related inhibitor screening and P-gp mediated or related transport drugs as disclosed in the cited articles that are incorporated by reference elsewhere in the description. Such a method of screening covers use of cells overexpressing BCRP to test for binding of inhibitor and/or to test whether a phannaceutically active compound is present in a lower amount in such a cell than a corresponding cell with an inactive BCRP transport system. If this is the case then active transport using BCRP is occurring. Subsequently, testing with other systems can eliminate or reveal participation of other drug transport mechanisms for the particular drug to be tested. Thus an additional means for sorting out various specificities for various drug transport mechanisms is provided.

The invention also covers animals in which the BCRP gene has been inactivated, such that no BCRP related or mediated transport that is measurable can be discerned. This can occur in mice for example as a test model for in vivo testing of the results of inactivated BCRP transport and also to test whether drug transport of the pharmaceutically active compound does or does not occur. The results in wild type animals, i.e. corresponding to the knock out animal with the exception of the inactivated BCRP transport system, can be compared with the results in the knock out animal to ascertain whether a BCRP related or mediated compound has been tested. Further details can be obtained by carrying out the test with other animals in which one or more MDR related transport systems have been eliminated. It is also possible to use systems in which one or more of the other MDR transport systems are solely active in order to ascertain information on specificity for the various transport systems. The person skilled in the art will recognise which systems from the prior art are suitable. Also on the basis of the data provided in the prior art a knock out system, e.g. using genetic modification, can be achieved. The gene information for murine BCRP is for example available and thus the route to a knock out BCRP mouse is derivable. Use of such a knock out mouse in screening is a particularly useful embodiment of the invention. To circumvent possible lethality problems the creloxP system can for example be used. This allows tissue specific or inducible inactivation of the target gene.

The resulting mice can be used in analysis of pharmacological effects in comparison to wild type mice. The knock out animals can be used as test models for assessing feasibility, efficacy and safety of BCRP related or mediated transport inhibition.

EXAMPLE 1

Cytotoxicity Assay

Cytotoxicity was Determined Using the Sulphorhodamine (SRB) Assay.

Cells were plated in 96-wells plates, 1500 cells/well. Cells were cultured for 48 h at 37° C. and 5% $CO_2$ in the absence of drugs. Then, in a serial dilution from approximately 1 µM to approximately 0.05 nM drugs were added, and cells were cultured for another 5 days at 37° C. and 5% $CO_2$ Next cells are fixated in the plate, washed, and coloured with SRB. After 20 min unbound SRB is washed away using 0.1 M acetic acid. SRB that is bound to the cells is dissolved in 10 mM Tris-HCl buffer. Using a 96-well plate reader the absorbance at 540 nm is measured. For each drug the $IC_{50}$ value was determined. Results are the mean of at least 3 experiments. The results are depicted in the following table.

From these results it is clear that under normal conditions the T8 cell-line has a lower sensitivity for topoisomerase I drugs, the IC50 values for T8 are higher than for IGROV1. The resistance factor (Rf), i.e. the IC50 for T8 devided by the IC50 value for IGROV1, varies from 11 for BNP1350 to 231 for SN-38.

If the cytotoxicity is determined in the presence of 2 µM of the BCRP inhibitor GF120918, the $IC_{50}$ values for the T8 resistent cell line exhibit a strong decrease. The cells become more sensitive towards the drugs by a factor of 1.4 to 24.4. It is important to notice that GF120918 has no or very little effect on the sensitivity of the parental cell line IGROV1, hence the effect for T8 can be ascribed to inhibition of BCRP by GF120918.

The Rf values in the presence of GF120918 are on average a factor 5 lower compared to the values in the absence of GF120918. By the addition of GF120918 the resistance of T8 for topoisomerase I drugs is for the greater part reversed.

TABLE

Cytotoxicity topoisomerase I drugs in IGROV1 parental and T8 resistant cells +/− 2 µM GF120918

|  | IGROV1 $IC_{50}$ (nM) | IGROV1 + GF120918 $IC_{50}$ (nM) | ratio −/+ GF120918 |
|---|---|---|---|
| topotecan | 8.93 | 9.23 | 0.97 |
| CPT11 | 543.77 | 651.02 | 0.84 |
| SN-38 | 1.82 | 1.10 | 1.66 |
| GG211 | 0.64 | 0.87 | 0.74 |
| DX8951f | 0.10 | 0.17 | 0.60 |
| BNP1350 | 0.44 | 0.84 | 0.53 |

|  | T8 $IC_{50}$ (nM) | Rf | T8 + GF120918 $IC_{50}$ (nM) | Rf | ratio −/+ GF120918 |
|---|---|---|---|---|---|
| topotecan | 978.52 | 110 | 40.16 | 4.3 | 24.4 |
| CPT11 | 33958.77 | 62 | 3037.67 | 4.7 | 11.2 |
| SN-38 | 419.21 | 231 | 6.54 | 6.0 | 64.1 |
| GG211 | 22.44 | 35 | 4.57 | 5.3 | 4.9 |
| DX8951f | 2.88 | 29 | 0.39 | 2.3 | 7.4 |
| BNP135O | 4.94 | 11 | 3.45 | 4.1 | 1.4 |

EXAMPLE 2

Determination of the Effect of GF120918 (GF120918) on the Oral Bioavailability of Topotecan.

Setup

To exclude effects of P-glycoprotein inhibition by GF120918, mdr1a/1b (−/−) mice were used in this experiment. First, mice were given orally GF120918 (50 mg/kg) or control substance at 15 min. prior to Topotecan administration. Subsequently, Topotecan was administered orally at a dose of 1 mg/kg. Finally, blood was collected at indicated time points. All time points represent three mice.

Animals

Animals were housed and handled according to institutional guidelines complying with Dutch legislation. The animals that were used in all experiments were mdr1a/1b (−/−) or wild-type mice of a 99% FVB genetic background, between 9–14 wk of age. All animals had free access to standard chow (AM-II, Hope Farms; Woerden, The Netherlands) and acidified water at a 12 h/12 h light/dark cycle and constant room temperature of 22° C.

Drug Preparation, Administration and Analysis

GF120918 was suspended in a hydroxypropylmethylcellulose (10 g/l): Tween 80 (2% v/v): $H_2O$ (0.5:1:98.5 v/v/v) formulation for oral administration, at 5 mg.ml$^{-1}$. Animals were treated with 50 mg.kg$^{-1}$ GF120918 or a corresponding amount of vehicle by gavage in a volume of 10 µl drug solution per gram body weight under a light Metofane (Mallinckrodt Veterinary, Mundelein, Ill., USA) anaesthesia. Topotecan (freshly prepared, in 5% D-glucose) was administered orally such that 5 µl of the appropriate solution was administered per gram body weight. Dosage was 1.0 mg.kg$^{-1}$ body weight. Animals were sacrificed at indicated time points by cardiac puncture or axillary bleeding after anaesthesia with metofane and at the same time blood was collected. Heparinized plasma was mixed with 3 volumes of cold methanol (−20° C.). Topotecan levels in plasma were determined by HPLC analysis as described by Rosing et al., 1995, J. Chromatography, 668: 107–115, and are depicted in FIG. 1.

Conclusion

Co-administration of a single oral dose of GF120918 results in a profoundly increased systemic exposure to oral topotecan. The increase in the area under the curve (AUC) is approximately 6 fold (see figure).

EXAMPLE 3

Figure 2:
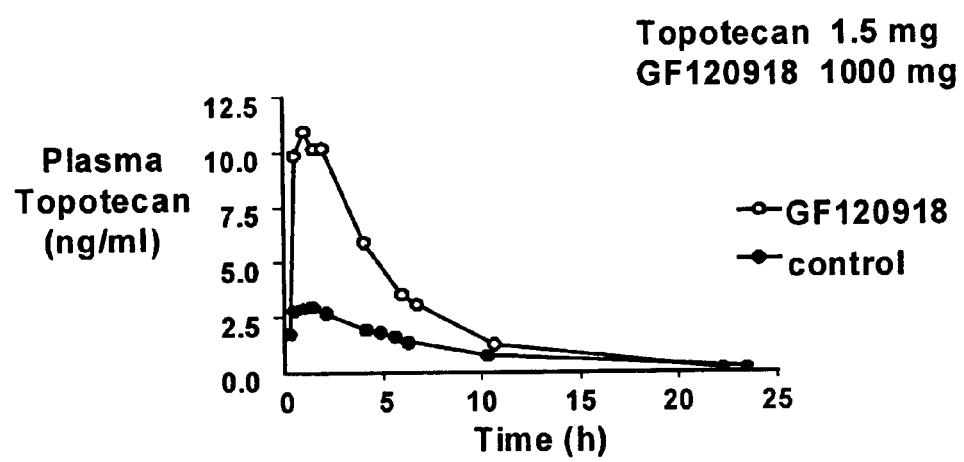
FIG. 2 is a graph of the topotecan levels over time in plasma as determined by HPLC both with and without GF120918.
Figure 3:
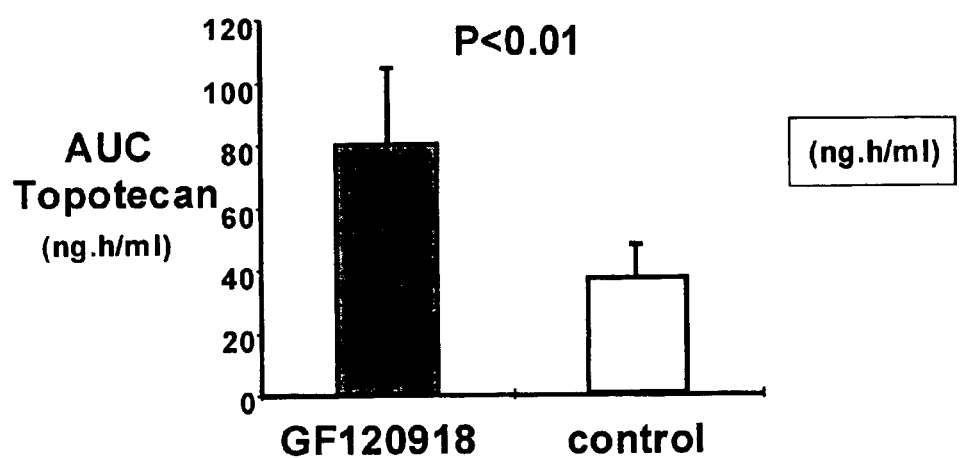
FIG. 3 is a graph of the area under the curve (AUC) showing increased systemic exposure to oral topotecan with the coadministration of oral GE120918.

In this example the first results of a clinical trial are shown. Three patients received topotecan orally at a dosis of 1.0 mg.m$^{-2}$. Topotecan was administered with or without GF120918 (1000 mg). For illustrative purposes, the plasma concentration vs. time is shown for one patient in FIG. 2. In FIG. 3 the average including the standard deviation is shown for all three patients. These results confirm the results obtained in vitro according to Example 1.

EXAMPLE 4

Initial studies are performed with the novel substances XR9051 and XR9576 (from Xenova) in mice cell lines which are resistant against mitoxantrone as a result of the overexpression of BCRP. These substances are considered alternatives of the already disclosed compound GF120918.

The invention claimed is:

1. A method for increasing the bioavailability of at least one orally administered pharmaceutically active compound, wherein said pharmaceutically active compound is selected from the group consisting of camptothecin and a cytostatic camptothecin derivative, said method comprising:
    orally administering an effective bioenhancing amount of GF120918, wherein said GF120918 and said at least one pharmaceutically active compound are concomitantly administered.

2. Method according to claim 1, wherein said GF120918 is administered simultaneously with said camptothecin or said cytostatic camptothecin derivative.

3. Method according to claim 1, wherein said GF120918 inhibits binding of ATP to a BCRP mediated and/or related drug transport protein.

4. Method according to claim 3, wherein the protein is BCRP.

5. Method according to claim 1, wherein said GF120918 and said camptothecin derivative are concomitantly administered.

6. Method according to claim 5, wherein said camptothecin derivative is selected from the group consisting of topotecan, GG211, DX8951f, BNP1350, 9-aminocamptothecin, 9-nitrocamptothecin, CPT11 and any metabolites thereof.

7. Method according to claim 6, wherein the metabolite is SN38.

8. Pharmaceutical composition comprising GF120918 and at least one pharmaceutically active compound, wherein said pharmaceutically active compound is selected from the group consisting of camptothecin and a camptothecin derivative.

9. A pharmaceutical composition, comprising:
    an effective amount of topotecan; and
    an effective amount of GF120918 to increase the bioavailability of said topotecan.

10. The pharmaceutical composition of claim 9, further comprising a pharmaceutically acceptable carrier suitable for oral administration.

11. A method for increasing the bioavailability of at least one orally administered pharmaceutically active compound, wherein said pharmaceutically active compound is selected from the group consisting of camptothecin and a cytostatic camptothecin derivative, comprising:
    orally administering an effective bioenhancing amount of GF120918, wherein said GF120918 and said at least one pharmaceutically active compound are present at overlapping periods of time.

12. The method according to claim 11, wherein the GF120918 is administered simultaneously with the camptothecin or cytostatic camptothecin derivative.

13. The method according to claim 11, wherein said camptothecin or cytostatic camptothecin derivative is topotecan.

* * * * *